(12) United States Patent
Muehlsteff et al.

(10) Patent No.: US 8,277,387 B2
(45) Date of Patent: Oct. 2, 2012

(54) SYSTEM AND METHOD FOR DETERMINING THE BLOOD PRESSURE OF A PATIENT

(75) Inventors: Jens Muehlsteff, Aachen (DE); Gerd Lanfermann, Aachen (DE); Xavier Aubert, Brussels (BE); Olaf Such, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 822 days.

(21) Appl. No.: 12/091,330

(22) PCT Filed: Oct. 13, 2006

(86) PCT No.: PCT/IB2006/053762
§ 371 (c)(1),
(2), (4) Date: Apr. 24, 2008

(87) PCT Pub. No.: WO2007/049174
PCT Pub. Date: May 3, 2007

(65) Prior Publication Data
US 2008/0287814 A1    Nov. 20, 2008

(30) Foreign Application Priority Data
Oct. 24, 2005   (EP) .................................... 05109882

(51) Int. Cl.
*A61B 5/02* (2006.01)
(52) U.S. Cl. ......... 600/490; 600/481; 600/483; 600/485
(58) Field of Classification Search ............ 600/481, 600/483, 485, 490
See application file for complete search history.

(56) References Cited

U.S. PATENT DOCUMENTS 4,924,871 A * 5/1990 Honeyager .................. 600/485
4,998,534 A * 3/1991 Claxton et al. ............... 600/483
(Continued)

FOREIGN PATENT DOCUMENTS
JP       2004164442 A    6/2004
(Continued)

OTHER PUBLICATIONS

Lass et al: "Continuous Blood Pressure Monitoring During Exercise Using Pulse Wave Transit Time Measurement"; Proceedings of the 26th Annual International Conference of the IEEE EMBS, San Francisco, CA, Sep. 1-5, 2004, pp. 2239-2242.
Bai et al: "Design of Home Health Care Network", 1995 IEEE-EMBC and CMBEC, Theme 7: Instrumentation, 1997 IEEE, pp. 1657-1658.
(Continued)

*Primary Examiner* — Charles A Marmor, II
*Assistant Examiner* — Michael D'Angelo

(57) ABSTRACT

In order to provide a technique for determining high-quality blood pressure values of a patient, especially in cases of unsupervised blood pressure measurements in a home environment, it is suggested to use a system (1) for determining the blood pressure of a patient (2) comprising a blood pressure measuring device (3, 4) for measuring a blood pressure value, an auxiliary device (6, 7, 8, 9) for measuring the motor activity of the patient (2) during a defined period of time prior to the blood pressure measurement, and a processing device (13, 14), said processing device (13, 14) being adapted to obtain the motor activity information and the blood pressure value, said processing device (13, 14) being further adapted to automatically assess the blood pressure value using the motor activity information, and said processing device (13, 14) being further adapted to provide a measuring result depending on the result of the assessment.

20 Claims, 2 Drawing Sheets

U.S. PATENT DOCUMENTS

| | | | |
|---|---|---|---|
| 5,014,714 A | | 5/1991 | Millay et al. |
| 5,042,496 A | * | 8/1991 | Sjonell .......................... 600/490 |
| 6,081,742 A | | 6/2000 | Amano et al. |
| 6,491,647 B1 | | 12/2002 | Bridger et al. |
| 6,498,652 B1 | * | 12/2002 | Varshneya et al. ............ 356/477 |
| 6,872,182 B2 | | 3/2005 | Kato et al. |
| 2004/0097815 A1 | | 5/2004 | Forstner |
| 2004/0199081 A1 | | 10/2004 | Freund et al. |
| 2005/0033188 A1 | | 2/2005 | Whitaker et al. |

FOREIGN PATENT DOCUMENTS

| WO | WO0241771 A1 | 5/2002 |
|---|---|---|

OTHER PUBLICATIONS

Fotiadis, D.: "A Wearable Platform for the Monitoring of Health Condition and Sport Performance and the Real-Time Prevention of Sport Injuries", University of Ioannina, Dept. of Computer Science, Unit of Medical Technology and Intelligent Information Systems, 17 Pages, Oct. 2002.

"Blood Pressure Monitors and Medical Home Blood Pressure Monitors"; New Zealand Medical & Science Limited, Advertising Brochure, 4 Pages, Found at www.NZMS.CO.NZ/BLOOD_PRESSURE.HTML, May 2005.

* cited by examiner

SYSTEM AND METHOD FOR DETERMINING THE BLOOD PRESSURE OF A PATIENT

The present invention relates to a system and method for determining the blood pressure of a patient. Furthermore, the invention relates to a computer program for determining the blood pressure of a patient.

Blood pressure is one of the most important physiological parameters and plays a major role as input variable in medical diagnostics, disease prevention as well as disease management systems. Blood pressure is an independent risk factor for cardiovascular disease and renal disease. In the US, in 2004, there were 65 million adults having hypertension with systolic pressure above 140 mmHg and diastolic pressure above 90 mmHg and/or using antihypertensive drugs. Additionally, one-quarter of US-adults show "prehypertension" symptoms. As these figures show, hypertension causes a strong social burden.

During the last years, new strategies in blood pressure monitoring and therapy have been proposed. Time-to-time blood pressure measurements at hospitals will be gradually supplemented with home-based personal healthcare systems, giving patients more freedom and improved quality of live. In this application area, it will be essential to get reliable, robust, vital parameters via unsupervised measurements, e.g. via continuous blood pressure monitoring at home. Unsupervised blood pressure measurements in personal healthcare applications (e.g. for home-based congestive heart failure management) are prone to measurement artifacts or handling errors due to inadequate operating conditions and/or patient non-compliance.

Despite the fact that the medical community gives recommendations for obtaining reliable blood pressure readings, almost no commercially available blood pressure measuring device controls whether or not the patient follows those recommendations. Therefore, there is a risk that, e.g., home-based disease management systems using state of the art technology solutions for blood pressure readings can give wrong therapy advice. This could result in rejection of home-based personal healthcare solutions by the medical community.

In US patent application 2004/0199081 A1, a method and device for measuring the blood pressure is described, in which a pressure sensor is applied to an individual's limb to detect the blood pressure prevailing in said limb. The orientation of the limb is detected during the measurement by means of an orientation sensing unit, and the detected blood pressure is corrected in an evaluating unit in response to the limb's detected orientation.

It is an object of the present invention to provide a technique for determining high-quality blood pressure values of a patient, especially in cases of unsupervised blood pressure measurements in a home environment.

This object is achieved, according to the invention, by a system for determining the blood pressure of a patient, comprising an auxiliary device for measuring the motor activity of the patient during a defined period of time prior to a blood pressure measurement, a blood pressure measuring device for measuring a blood pressure value, and a processing device, said processing device being adapted to obtain the motor activity information and the blood pressure value, said processing device being further adapted to automatically assess the blood pressure value using the motor activity information, and said processing device being further adapted to provide a measuring result depending on the result of the assessment.

The object of the present invention is also achieved by a method of determining the blood pressure of a patient, comprising the steps of measuring the motor activity of the patient during a defined period of time prior to a blood pressure measurement, measuring a blood pressure value, automatically assessing the blood pressure value using the motor activity information, and providing a measuring result depending on the result of the assessment.

The object of the present invention is also achieved by a computer program for determining the blood pressure of a patient, the program comprising computer instructions to automatically assess a measured blood pressure value using motor activity information of the patient, said motor activity information being obtained during a defined period of time prior to a blood pressure measurement, and computer instructions to provide a measuring result depending on the result of the assessment, when the computer program is executed in a computer. The technical effects necessary according to the invention can thus be realized on the basis of the instructions of the computer program in accordance with the invention. Such a computer program can be stored on a carrier, such as a CD-ROM, or it can be available over the internet or another computer network. Prior to executing the computer program, it is loaded into the computer by reading the computer program from the carrier, for example by means of a CD-ROM player, or from the internet, and storing it in the memory of the computer. The computer includes, inter alia, a central processor unit (CPU), a bus system, memory means, e.g. RAM or ROM etc., storage means, e.g. floppy disk or hard disk units etc. and input/output units. Alternatively, the inventive method could be implemented in hardware, e.g. using one or more integrated circuits.

It is known that an incorrect (increased) blood pressure value is likely to be measured if the patient does not sit quietly for at least 5 to 10 minutes before the blood pressure reading is taken. In other words, the patient should be at rest for at least 5 to 10 minutes before the measurement. A core idea of the invention is to employ information about the patient's motor activity prior to the blood pressure measurement for automatically assessing the quality of the subsequently measured blood pressure values. In other words, the trustworthiness of these values is automatically determined. For this purpose, measurements of the patient's motor activity are performed prior to the blood pressure measurement. "Motor activity" in particular comprises the physical activity of the patient. The invention employs the quality information in order to decide whether or not the measured blood pressure value can be treated as "valid" or "trustworthy". The invention cannot only be used in a home environment. In a hospital or the like, the invention can help young and inexperienced, or even unskilled, staff to obtain high-quality blood pressure values.

In order to carry out the invention, an auxiliary device for measuring the motor activity of the patient is provided. Preferably, the auxiliary device is adapted for continuous long-term monitoring of the patient's motor activity. For example, a number of distributed body-worn acceleration sensors can be employed for measuring the motor activity of the patient. The acceleration sensors are preferably integrated into a garment or textile worn by the patient.

Generally any type of blood pressure measuring device can be used with the invention. There are several established methods and devices providing blood pressure values, e.g. the use of sphymomanometers (auscultatory method), oscillometric techniques (the most widespread technique for self measurement), PTT (pulse transmit time) techniques, tonometry or the finger cuff method of Penaz. In the present invention, preferably an oscillometric technique is used, in which the patient uses a blood pressure cuff to be fixed e.g. around the patient's arm.

The processing device preferably comprises a computer means, e.g. a microprocessor with input/output means for performing the processing of blood pressure data and additional measuring-related information. The processing device is preferably a body-worn device, which communicates with sensors, measuring devices and other devices employed in the present invention via a communication system. Preferably, all devices are adapted to use a wireless communication system, e.g. BLUETOOTH or WLAN or the like. For this purpose, all sensors, measuring devices and other devices communicating with the processing device comprise a transmitter or transceiver unit.

These and other aspects of the invention will be further elaborated on the basis of the following embodiments, which are defined in the dependent claims.

In a preferred embodiment of the invention, the auxiliary device is adapted to measure the motor activity of the patient during the blood pressure measurement. Thus, the motor activities cannot only be observed prior to, but also during, the reading process. All movements carried out by the patient during the measurement can be taken into account when assessing the quality of the measurement.

The processing device is preferably adapted to provide a measuring result in form of a corrected blood pressure value and/or in form of a blood pressure value with a confidence interval or in form of a signal to the patient (e.g. via a monitor or speaker etc., connected or connectable to the processing unit) requesting the patient to repeat the blood pressure measurement. In other words, with the present invention a measured blood pressure value can be corrected and/or a confidence value can be added to a blood pressure value or it can be decided that a reading has to be discarded and the measurement has to be repeated, all these steps being performed depending on the result of the assessment, i.e. depending on the evaluated quality of the blood pressure measurement. Correction of a measured blood pressure value is preferably performed using the measuring-related information, for example using the motor activity of the patient before or during the blood pressure measurement.

Besides the motor activity of the patient prior to the blood pressure measurement, there are a number of additional measuring-related (context) factors, which can influence the quality of the measurement and thus the quality of the measured blood pressure values. Therefore, according to another embodiment of the invention, it is suggested to provide a number of additional auxiliary devices, said additional auxiliary devices being adapted to provide additional measuring-related information, which has been obtained before and/or during the blood pressure measurement, and the processing device is adapted to obtain at least one piece of additional measuring-related information for assessing the blood pressure value. By using more than just one piece of measuring-related information, it is possible to achieve much more reliable and high-quality measuring results. The additional measuring-related information is provided by means of additional auxiliary devices, e.g. personal healthcare equipment in the surroundings of the patient, like body-worn sensors, sensors in the measurement room, and/or via the internet. However, some or even all of the measuring-related information used in the assessing process can be provided by the blood pressure measuring device itself. For this purpose, the blood pressure measuring device may include one or more auxiliary devices.

In a preferred embodiment of the invention, all data processing is carried out by the processing unit. However, some measuring-related data, including the motor activity data and additional measuring-related data, may be (pre)processed by the relevant auxiliary device, sensor or other device, before being transmitted to the processing unit for assessing the blood pressure value. For this purpose, the relevant sensors, measuring devices and other devices employed in the present invention comprise a (pre)processing unit, which may include an analog-to-digital converter and a digital signal processor.

According to the invention, the measuring-related information additionally used can be classified into four groups of data: patient-related measuring data, non-patient-related measuring data, patient-related non-measuring data and non-patient-related non-measuring data. Patient-related data is data which is affected directly or indirectly by the patient. Non-patient-related data is data which is not affected by the patient. Measuring data is data which can be measured directly using sensors etc., and non-measuring data is data which cannot be measured directly, but which can be obtained, e.g., via databases etc.

The motor activity of the patient is patient-related measuring data. Other patient-related measuring data, which preferably is included into the assessing process, is ECG (electrocardiogram) data of the patient. Using such ECG data, e.g. the patient's heart rate, heart rhythm, heart rate variability and respiration rate etc., can be utilized for assessing the quality of the reading. For example, the patient's mental state can be estimated using an appropriate algorithm from the patient's heart rate before and/or during the blood pressure measurement. For this purpose, preferably a body-worn ECG device is provided. The ECG electrodes are preferably integrated into the same garment or textile which carries the motor activity sensors.

In another embodiment of the invention, the galvanic skin response of the patient is measured for estimating the patient's mental stress (e.g. white coat syndrome). Again, this measurement can be performed before and/or during the blood pressure measurement. The electrodes employed for this purpose are preferably integrated into the blood pressure measuring device or into the same garment or textile which carries the motor activity sensors and the ECG electrodes.

Beyond these physiological data, it is preferably controlled whether the patient speaks or remains silent during the blood pressure measurement. For a high-quality measuring result the patient should not talk during the measurement. To control the patient's silence a microphone or the like is employed. Again, the microphone is preferably also integrated into said garment or textile.

In another preferred embodiment of the invention, a device for measuring the patient's posture during the blood pressure measurement is provided. For a high-quality measuring result, the patient should be seated comfortably, the patient's legs should not be crossed and the patient's arm wearing the cuff should be supported at heart level. To control the patient's posture, preferably, a camera system with integrated image-processing is employed as an auxiliary device.

Other factors (patient-related measuring data), which can additionally be included into the assessing process are the position of the cuff during the blood pressure measurement (the cuff should encircle at least 80% of the circumference of the patient's arm), the patient's muscle activity during the blood pressure measurement (the muscles should be relaxed), drug admission before the blood pressure measurement, the patient's body composition, especially water, muscle and fat content to be measured using a scale, and the fact whether or not the patient is well rested.

For obtaining patient-related non-measuring data, the system preferably comprises a device for obtaining the sex and/or the age of the patient and/or a device for obtaining the history of blood pressure measurements of the patient. These devices are preferably adapted to obtain information from databases via a data communication system, e.g. via the internet. The obtained information can give further assistance for assessing the quality of the blood pressure measurement. Former measuring results can, for example, be used by the processing unit to validate current measuring results.

For obtaining non-patient-related measuring data, the system preferably comprises a
device for measuring the ambient (room) temperature during the blood pressure measurement and/or a device for measuring the ambient sound intensity during the blood pressure measurement. For a high-quality measuring result, the room should be at a comfortable temperature and the room should be quiet and free of distractions. For these measurements a thermometer and a microphone can be used. Thermometer and microphone are preferably integrated in the above-mentioned garment or textile. If, for example, the room temperature diverges from a "standard" temperature, the processing unit can correct the measured blood pressure value using, e.g., a standard calibration model or a patient-specific calibration table.

For obtaining non-patient-related non-measuring data, the system preferably comprises a device for obtaining the time of day (e.g. by using the built-in clock of the processing device) and/or a device for obtaining weather data (e.g. by using a connection to a local weather database via the internet).

Preferably, the system for determining the blood pressure of a patient is part of a disease management system or another (home-based) personal healthcare solution, which issues therapy decisions to the patient. With the present invention, the risk of using a wrong blood pressure value as input variable for such a disease management system can reliably be avoided.

These and other aspects of the invention will be described in detail hereinafter, by way of example, with reference to the following embodiments and the accompanying drawings, in which.

Figure 1:
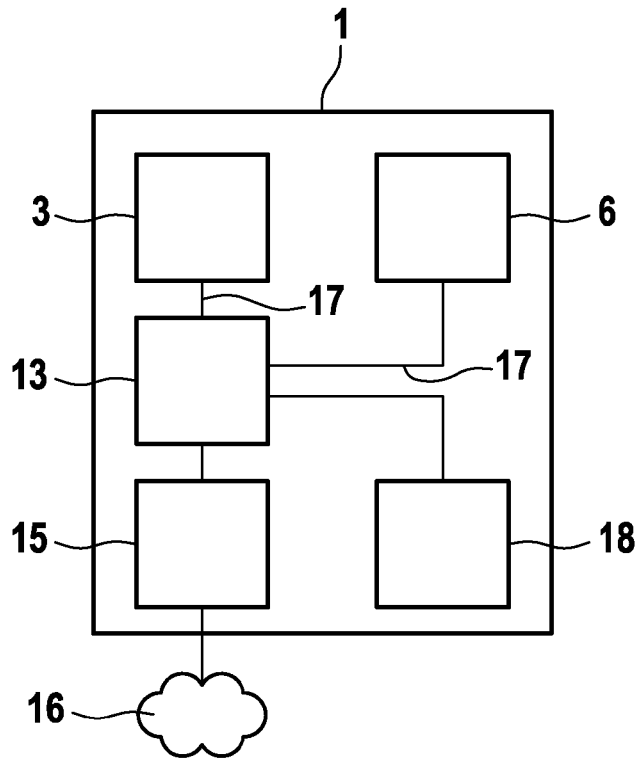
FIG. 1 shows a schematic block diagram of a system according to the invention.
Figure 2:
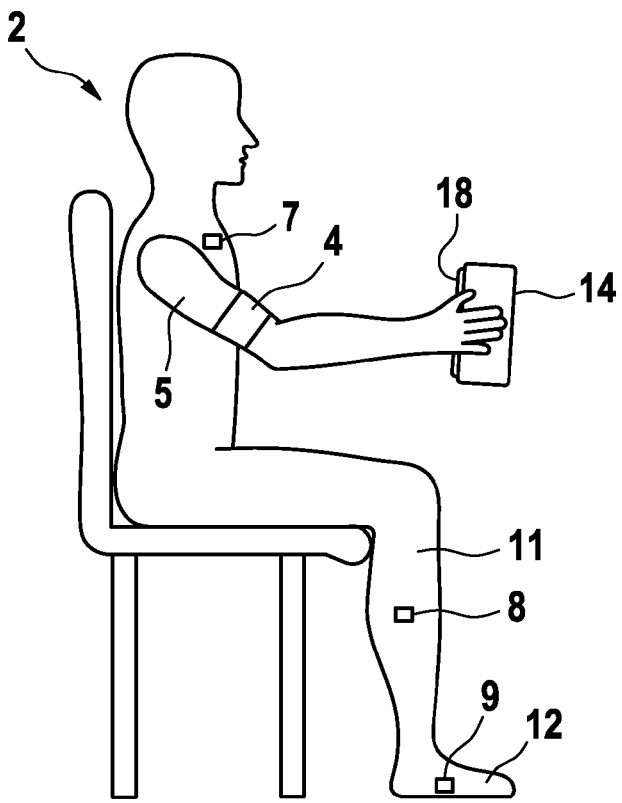
FIG. 2 shows a schematic illustration of a patient using the system.
Figure 3:
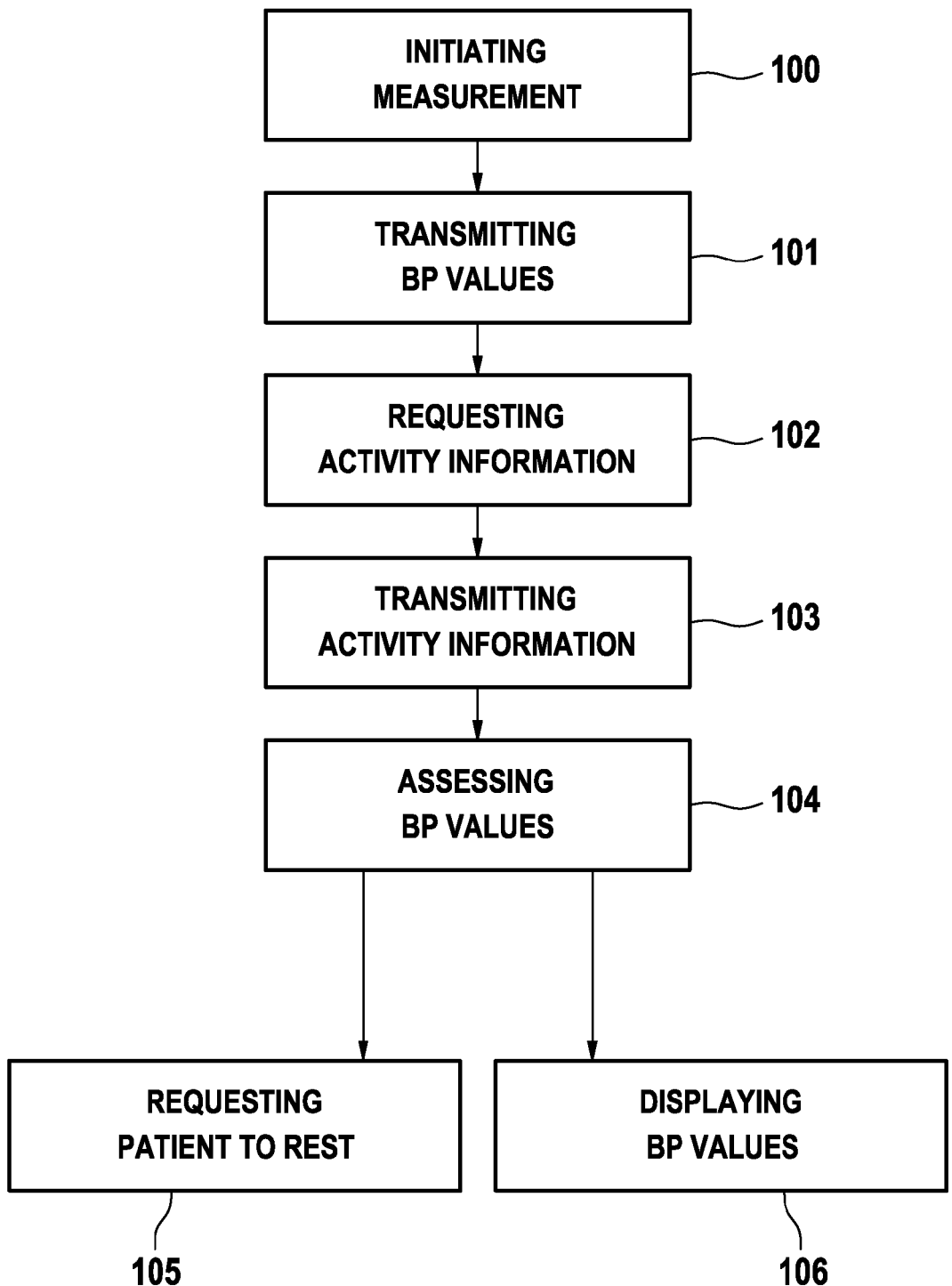
FIG. 3 shows a simplified flowchart of the method according to the invention.

The system 1 for determining the blood pressure of a patient 2 comprises a blood pressure measuring device 3 for measuring a blood pressure value. The blood pressure measuring device 3 operates using the oscillometric method. The blood pressure measuring device 3 comprises, inter alia, a cuff 4 positioned around the patient's upper arm 5.

The system 1 for determining the blood pressure further comprises a device 6 for measuring the motor activity of the patient 2 during a defined period of time prior to a blood pressure measurement. For this purpose, a number of body-worn activity sensors 7, 8, 9 are employed, which continuously measure movements of the patient 2. As activity sensors 7, 8, 9, three two-dimensional acceleration sensors are used. The sensors 7, 8, 9 are integrated into a garment (not shown) worn by the patient 2 in such a way that the first activity sensor 7 is positioned on the patient's shoulder, the second activity sensor 8 is positioned on the patient's lower leg 11 and the third activity sensor 9 is positioned on the patient's foot 12.

The system 1 for determining the blood pressure further comprises a processing device 13. The processing device 13 is part of a handheld computer system 14. The handheld computer system 14 comprises functional modules or units, which are implemented in form of hardware, software or in form of a combination of both. All data handling and data processing, the automatic assessment of the blood pressure values and the providing of a measuring result depending on the result of the assessment are achieved, according to the invention, by means of computer software comprising computer instructions adapted for carrying out the steps of the inventive method, when the software is executed in the handheld computer system 14.

In particular the handheld computer system 14 is adapted to obtain the motor activity information and the blood pressure value. For this purpose, the handheld computer system 14 as well as the blood pressure measuring device 3 and the acceleration sensors 7, 8, 9 are adapted to communicate with each other via a wireless communication system using sender and transmitter units (not shown). These sender and transmitter units are integrated parts of the handheld computer system 14, the blood pressure measuring device 3 and the acceleration sensors 7, 8, 9.

The handheld computer system 14 further comprises an interface 15 to communicate with other computer systems via the internet 16, e.g. with a server system at a hospital site in order to automatically transmit critical situations, like a critical hypertension, to a physician.

A typical measuring procedure is as follows: In a first step 100, the patient 2 initiates a blood pressure measurement and the measurement is performed. In a next step 101, the blood pressure values are transmitted to the processing unit 13 using a wireless communication link 17. In a subsequent step 102, the processing unit 13 (triggered by the receiving of the blood pressure values) communicates with all acceleration sensors 7, 8, 9, using a wireless communication link 17, in order to request information about the patient's motor activity during the last ten minutes prior to the blood pressure measurement. Accordingly, in a next step 103, the acceleration sensors 7, 8, 9 send motor activity data to the processing unit 13 using said communication link 17. In a next step 104, the processing unit 13 assesses the obtained blood pressure values using the motor activity information by means of the computer software which comprises appropriate algorithms. If the activity level given by at least one acceleration sensor 7, 8, 9 of the patient 2 is found (according to an internal look-up table) to be too high during a defined period of time, e.g. the last five minutes, the processing device 13 generates and sends a signal, in a subsequent step 105, to a user interface, e.g. a monitor 18 of the handheld computer system 14, requesting the patient 2 to rest for an appropriate time and to repeat the blood pressure measurement afterwards. If the activity level of the patient 2 is found to be regular, the processing device 13 calculates a confidence interval (e.g. ±5 mm Hg) for the blood pressure value and, in a subsequent step 106, sends both pieces of information to the monitor 18 of the handheld computer system 14 for display to the patient 2.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and non-restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit, may fulfill the functions of several means recited in the claims. Any reference signs in the claims shall not be construed as limiting the claim concerned.

Reference Numerals
1 system
2 patient
3 blood pressure measuring device
4 cuff
5 upper arm
6 device for measuring motor activity
7 activity sensor
8 activity sensor
9 activity sensor
10 (free)
11 lower leg
12 foot
13 processing device
14 handheld computer system
15 interface
16 internet
17 wireless communication link
18 monitor

The invention claimed is:

1. A system for determining blood pressure of a patient, comprising:
   a blood pressure measuring device for measuring a blood pressure value;
   an auxiliary device for measuring motor activity of the patient during a defined period of time prior to the blood pressure measurement; and
   a processing device, said processing device being configured to obtain the motor activity information and the blood pressure value, said processing device being further configured to automatically make a determination whether the blood pressure value is reliable based on whether the motor activity information is at or below a predefined level stored in a look-up table, and said processing device being further configured to provide a measuring result based on the determination.

2. The system as claimed in claim 1, wherein the auxiliary device is configured to measure the motor activity of the patient during the blood pressure measurement.

3. The system as claimed in claim 1, wherein the processing device is configured to provide a measuring result in form of a corrected blood pressure value.

4. The system as claimed in claim 1, wherein the processing device is configured to provide a measuring result in form of a blood pressure value with a confidence interval.

5. The system as claimed in claim 1, wherein the processing device is configured to provide a measuring result in form of a signal to the patient requesting the patient to repeat the blood pressure measurement.

6. The system as claimed in claim 1, further comprising a number of additional auxiliary devices, said additional auxiliary devices being configured to provide additional measuring-related information which has been obtained before or during the blood pressure measurement, and the processing device being configured to obtain at least one additional piece of measuring-related information for making the determination of the reliability of the blood pressure value.

7. The system as claimed in claim 6, wherein said additional auxiliary device comprises a device for measuring ECG data of the patient.

8. The system as claimed in claim 6, wherein said additional auxiliary device comprises a device for measuring the galvanic skin response of the patient.

9. The system as claimed in claim 6, wherein said additional auxiliary device comprises a device for measuring the patient's silence.

10. The system as claimed in claim 6, wherein said additional auxiliary device comprises a device for measuring the patient's posture.

11. The system as claimed in claim 6, wherein said additional auxiliary device comprises a device for obtaining the sex or age of the patient.

12. The system as claimed in claim 6, wherein said additional auxiliary device comprises a device for obtaining the history of blood pressure measurements of the patient.

13. The system as claimed in claim 6, wherein said additional auxiliary device comprises a device for measuring the ambient temperature during the blood pressure measurement.

14. The system as claimed in claim 6, wherein said additional auxiliary device comprises a device for measuring the ambient sound intensity.

15. The system as claimed in claim 6, wherein said additional auxiliary device comprises a device for obtaining the time of day.

16. The system as claimed in claim 6, wherein said additional auxiliary device comprises a device for obtaining weather data.

17. A method of determining blood pressure of a patient, comprising the steps of:
   measuring motor activity of the patient using an auxiliary device during a defined period of time prior to a blood pressure measurement;
   measuring a blood pressure value using a blood pressure measuring device;
   automatically making a determination whether the blood pressure value is reliable based on whether the motor activity information is at or below a predefined level stored in a look-up table; and
   providing a measuring result based on the determination.

18. The method as claimed in claim 17, wherein measuring the motor activity of the patient is performed during the blood pressure measurement.

19. The method as claimed in claim 17, wherein the determination of whether the blood pressure value is reliable is performed using a number of additional measuring-related pieces of information, which have been obtained before or during the blood pressure measurement.

20. A computer-readable medium containing computer executable instructions, that when executed on a computer, cause the computer to determine blood pressure of a patient, the instructions comprising:
   automatically making a determination of a reliability of a measured blood pressure value based on whether motor activity information of the patient is at or below a predefined level stored in a look-up table, said motor activity information being obtained during a defined period of time prior to a blood pressure measurement; and
   providing a measuring result depending on the determination.

* * * * *